United States Patent [19]

Kaiser

[11] 4,172,959
[45] Oct. 30, 1979

[54] PROCESS FOR THE MANUFACTURE OF DIPHENYL ETHERS

[75] Inventor: Klaus H. Kaiser, Hofheim am Taunus, Fed. Rep. of Germany

[73] Assignee: Hoechst Aktiengesellschaft, Frankfurt am Main, Fed. Rep. of Germany

[21] Appl. No.: 862,663

[22] Filed: Dec. 21, 1977

[30] Foreign Application Priority Data

Dec. 23, 1976 [DE] Fed. Rep. of Germany ....... 2658496

[51] Int. Cl.² ............................................. C07C 41/04
[52] U.S. Cl. .................................... 568/637; 568/586
[58] Field of Search .................... 260/613 R; 568/586, 568/637

[56] References Cited
FOREIGN PATENT DOCUMENTS 757218 4/1971 Belgium.
754053 6/1975 South Africa.
337379 6/1972 U.S.S.R..

OTHER PUBLICATIONS

Z. Obsc. Chim., vol. 34 (1964), 10, 3390.
Z. Org. Chim., vol. 1, (1965), 5, 901.
Gould, Mechanism and Structure in Organic Chemistry, (1959), 216–219.
McBee et al., J.A.C.S., vol. 73 (1951), 1325–1326.

Primary Examiner—Bernard Helfin
Attorney, Agent, or Firm—Curtis, Morris & Safford

[57] ABSTRACT

Hydroquinone mono-phenyl ethers, and their alkali metal salts of the formula

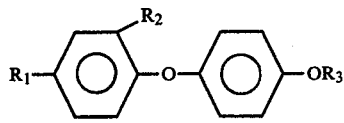

in which one of the radicals $R_1$ and $R_2$ denotes trifluoromethyl and the other denotes hydrogen or halogen and $R_3$ represents hydrogen or an alkali metal cation or ammonium cation are prepared by reacting hydroquinone bis-phenyl ethers (bisphenoxybenzenes) of the formula

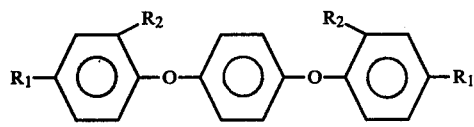

with hydroquinone derivatives of the formula

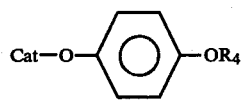

in which Cat denotes an alkali metal cation or ammonium cation and $R_4$ denotes an alkali metal cation or ammonium cation or a $(C_1-C_4)$-alkyl group, in a polar aprotic solvent at temperatures from 120° to 280° C., and optionally, an alkyl group present in the $R_4$-position is split off by treatment with an acid.

5 Claims, No Drawings

PROCESS FOR THE MANUFACTURE OF DIPHENYL ETHERS

In the manufacture of hydroquinone mon-phenyl ethers by reacting alkali metal salts of hydroquinone with substituted halogenobenzenes, the corresponding bis-phenyl ethers are in general obtained as undesired by-products in varying amounts, depending on the reaction procedure. There is a need to convert by-products of this type into a form which can be used industrially.

It has already been disclosed that diaryl ethers which carry, on one phenyl ring, a nitro group in the o-position or p-position relative to the other ether bond, can be trans-etherified or split using nucleophilic reagents, such as potassium phenolates, potassium alcoholates, potassium hydroxide or ammonia, in suitable solvents (Russian Patent Specification No. 337,379; Z. Obsc. Chim. 34 (1964), 10, 3390; Z. Org. Chim. 1, (1965), 5, 901; and Belgian Patent Specification No. 757,218).

Corresponding trans-etherifications or splitting of diaryl ethers or bis-ethers which carry a trifluoromethyl group as a substituent in one phenyl ring have not hitherto been disclosed.

The invention thus relates to a process for the manufacture of hydroquinone mono-phenyl ethers, and their alkali metal salts, of the general formula

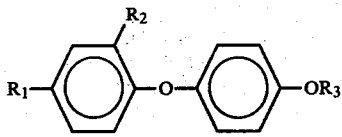

in which one of the radicals $R_1$ and $R_2$ denotes trifluoromethyl and the other denotes hydrogen or halogen and $R_3$ represents hydrogen or an alkali metal cation or ammonium cation, wherein hydroquinone bis-phenyl ethers (bisphenoxybenzenes) of the general formula

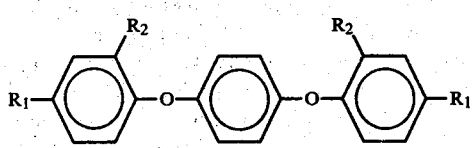

are reacted with hydroquinone derivatives of the general formula

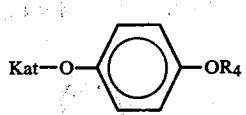

in which Cat denotes an alkali metal cation or ammonium cation and $R_4$ denotes an alkali metal cation or ammonium cation or a $(C_1-C_4)$-alkyl group, in a polar aprotic solvent at temperatures from 120° to 280° C., and, optionally, an alkyl group present in the $R_4$-position is split off by treatment with an acid.

The reaction according to the invention formally proceeds according to the following overall equation:

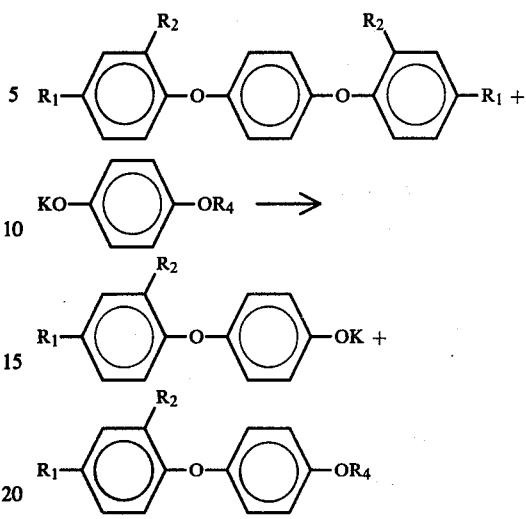

A preferred radical $R_1$ is —$CF_3$ and preferred radicals $R_2$ are hydrogen and chlorine or bromine. A preferred radical $R_4$ in formula III is $R_4$=Cat, potassium or sodium, in particular potassium, being preferred as the alkali metal.

Aprotic polar solvents are used, such as, for example, dimethylsulfoxide, dimethylformamide, dimethylacetamide, diethylacetamide, hexamethyl-phosphoric acid tris-amide, tetramethylsulfone, tetramethylurea, N-methylpyrrolidone or nitriles, such as acetonitrile or propionitrile. Dimethylsulfoxide and N-methylpyrrolidone are preferred. It is advantageous to carry out the reactions as far as possible in the absence of water, so that water formed, for example in the manufacture of the alkali metal salts, should be removed in the customary manner, such as, for example, by azeotropic or simple distillation or by adding a water-binding substance.

Possible reaction temperatures are those from 120° to 280° C., and temperatures from 160° to 260° C. are preferred. In order to achieve the desired reaction temperature, the reaction must be appropriately carried out under elevated (autogenous) pressure in a closed vessel.

In general, the reactants are employed in approximately stoichiometric amounts, an excess of one or other of up to 50%, in particular of up to 10%, being possible.

The amount of solvent is chosen so that the reaction mixture remains easily stirrable. It can be, for example, between 2 and 10 parts by weight, relative to the compound of the formula II.

After the reaction has ended, which in general requires between 2 and 20 hours, the reaction product is isolated in the customary manner, for example by filtering off the resulting salt and/or distilling off the solvent or by pouring the mixture into water and ice and acidifying the aqueous phase and then extracting it with an organic solvent.

The compounds of formula I obtained from them are valuable precursors for the manufacture of selective grass herbicides.

It is a particular advantage of the process according to the invention that two molecules of the formula I are formed from one molecule of the symmetric bis-ether of the formula II, and at the same time the part split off from the molecule II is also obtained in a form which can be used directly in the same manner as the main part.

The examples which follow are intended to illustrate the invention without limiting it.

EXAMPLE 1

4-Trifluoromethyl-4'-hydroxy-diphenyl ether 11.2 g (0.2 mole) of KOH in 11.2 g of water are added to 11.0 g (0.1 mole) of hydroquinone in 200 g of dimethylsulfoxide. The water is distilled off in vacuo. Thereafter, 39.8 g (0.1 mole) of 1,4-bis-(4-trifluoromethylphenoxy)-benzene are added and the reaction mixture is stirred at a temperature of 170° C. for 8 hours. The solvent is distilled off in vacuo, water is added to the residue and the mixture is acidified with 30 ml of concentrated HCl. The organic phase is separated off, the aqueous phase is extracted with methylene chloride and the combined organic phases are dried over Na$_2$So$_4$ and distilled.

34.2 g (0.134 mole) of 4-trifluoromethyl-4'-hydroxydiphenyl ether of melting point 46°–49° C. are obtained, corresponding to a yield of 67% of theory.

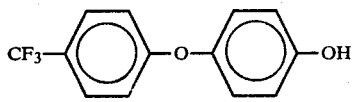

EXAMPLE 2

4-Trifluoromethyl-4'-hydroxy-diphenyl ether

If the solvent of Example (1) is replaced by N-methylpyrrolidone, 22.3 g of 4-trifluoromethyl-4'-hydroxy-diphenyl ether of melting point 46°–49° C. are obtained, corresponding to a yield of 44% of theory.

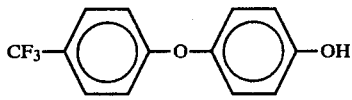

EXAMPLE 3

4-Trifluoromethyl-4'-hydroxy-diphenyl ether 81.5 g (0.2 mole) of NaOH in 8.15 g of water are added to 11.0 g (0.1 mole) of hydroquinone in 200 g of dimethylsulfoxide. The water is distilled off in vacuo. Thereafter, 39.8 g of 1,4-bis-(4-trifluoromethyl-phenoxy)-benzene are added and the reaction mixture is stirred at a temperature of 170° C. for 8 hours. Working up is carried out as in Example (1).

23.1 g (0.091 mole) of 4-trifluoromethyl-4'-hydroxydiphenyl ether of melting point 46°–49° C. are obtained, corresponding to a yield of 45% of theory.

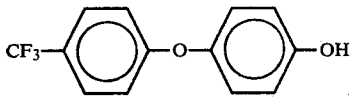

EXAMPLE 4

2-Chloro-4-trifluoromethyl-4'-hydroxy-diphenyl ether 11.2 g (0.2 mole) of KOH in 11.2 g of water are added to 11.0 g (0.1 mole) of hydroquinone in 200 g of dimethylsulfoxide. The water is distilled off in vacuo. Thereafter, 46.7 g (0.1 mole) of 1,4-bis-(2-chloro-4-trifluoromethylphenoxy)-benzene are added and the reaction mixture is stirred at a temperature of 167° C. for 8 hours. Working up is carried out as in Example (1). 31.9 g (0.111 mole) of 2-chloro-4-trifluoromethyl-4'-hydroxydiphenyl ether of melting point 42°–46° C. are obtained, corresponding to a yield of 55% of theory.

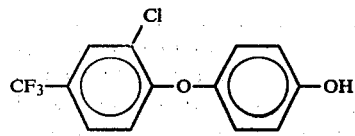

EXAMPLE 5

2-Trifluoromethyl-4'-hydroxy-diphenyl ether 11.2 g (0.2 mole) of KOH in 11.2 g of water are added to 11.0 g (0.1 mole) of hydroquinone in 200 g of dimethylsulfoxide. The water is distilled off in vacuo. Thereafter, 39.8 g (0.1 mole) of 1,4-bis-(2-trifluoromethyl-phenoxy)-benzene are added and the reaction mixture is stirred at a temperature of 170° C. for 14 hours. Working up is carried out as in Example (1). 23.4 g (0.092 mole) of boiling point 0.15 122° C. are obtained, corresponding to a yield of 46% of theory.

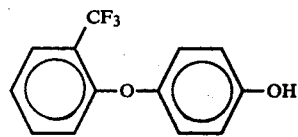

EXAMPLE 6

4-Trifluoromethyl-4'-methoxy-diphenyl ether and 4-trifluoromethyl-4'-hydroxy-diphenyl ether 5.6 g (0.1 mole) of KOH in 5.6 g of water are added to 12.4 g (0.1 mole) of 4-hydroxyanisole in 200 g of dimethylsulfoxide. The water is distilled off in vacuo. Thereafter, 39.8 g of 1,4-bis-(4-trifluoromethyl-phenoxy)-benzene are added and the reaction mixture is stirred at a temperature of 166° C. for 20 hours. The solvent is distilled off in vacuo. Water is added to the residue, and (a) the aqueous phase is extracted with methylene chloride. The organic phase is dried with Na$_2$SO$_4$ and distilled. 14 g (0.052 mole) of 4-trifluoromethyl-4'-methoxy-diphenyl ether of melting point 37°–38° C. are obtained, corresponding to 52% of theory.

(b) the aqueous phase is acidified with 30 ml of concentrated HCl and extracted with methylene chloride. The organic phase is dried with Na$_2$SO$_4$ and distilled. 15 g of 4-trifluoromethyl-4'-hydroxy-diphenyl ether of melting point 46°–49° C. are obtained, corresponding to 59% of theory.

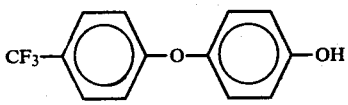

EXAMPLE 7

4-Trifluoromethyl-4'-hydroxy-diphenyl ether 39.8 g (0.1 mole) of 1,4-bis-(4-trifluoromethylphenoxy)-benzene are added to 6.2 g (0.11 mole) of sodium methylate in 200 g of dimethylsulfoxide and the mixture is stirred at a temperature of 180° C. for 12 hours. The solvent is distilled off in vacuo. Water is added to the residue and the mixture is acidified with 30 ml of concentrated hydrochloric acid. The organic phase is separated off, the aqueous phase is extracted with methylene chloride and the combined organic phases are dried with $Na_2SO_4$ and distilled. 6.3 g (0.025 mole) of 4-trifluoromethyl-4'-hydroxy-dipenyl ether of melting point 46°–49° C. are obtained, corresponding to a yield of 25% of theory.

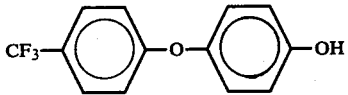

What is claimed is:

1. A process for the manufacture of hydroquinone mono-phenyl ethers and their alkali metal salts of the general formula:

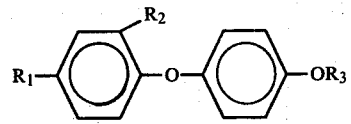

wherein one of the radicals $R_1$ and $R_2$ represents trifluoromethyl and the other represents hydrogen or halogen, and $R_3$ represents hydrogen or an alkali metal cation or ammonium cation, which process comprises reacting a bis-phenoxybenzene of the general formula:

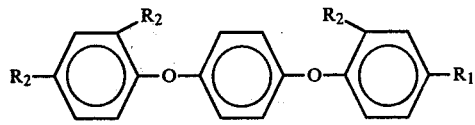

with a hydroquinone derivative of the general formula

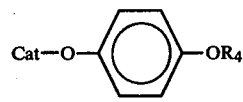

in which Cat represents an alkali metal cation or ammonium cation and $R_4$ represents an alkali metal cation, ammonium cation or $(C_1-C_4)$-alkyl group, in a polar aprotic solvent at a temperature of 120° to 280° C.

2. Process according to claim 1, wherein the reaction is carried out at temperatures from 160° to 260° C.

3. Process according to claim 1, wherein the reaction is carried out in a closed vessel.

4. Process according to claim 1, wherein dimethylsulfoxide or N-methylpyrrolidone is used as the solvent.

5. A process according to claim 1 wherein $R_4$ is alkyl and the $R_4$ group is split off by treatment with an acid to form said hydroquinone mono-phenyl ether.

* * * * *